United States Patent [19]

Possani et al.

[11] Patent Number: 4,929,718

[45] Date of Patent: May 29, 1990

[54] SYNTHETIC NOXIUSTOXIN RELATED PEPTIDES

[75] Inventors: Lourival D. P. Possani; Georgina B. Gurrola, both of Cuernavaca; Marco A. A. C. Bayon; Maria B. Sitges, both of Mexico, all of Mexico

[73] Assignee: Universidad Nacional Autonoma De Mexico, Dependence, Mexico

[21] Appl. No.: 132,169

[22] Filed: Dec. 14, 1987

[51] Int. Cl.[5] .......................... C07K 7/06; C07K 7/08

[52] U.S. Cl. .................................. 530/326; 530/328; 530/324; 530/858

[58] Field of Search ............... 530/324, 858, 328, 326; 514/12

[56] References Cited

U.S. PATENT DOCUMENTS 4,499,080 2/1985 Duflot et al. ........................ 530/324

OTHER PUBLICATIONS

L. D. Possani et al., Carlsburg Res. Commun., "Primary Structure of Noxiustoxin", 47: 285–289, 1982.

Anthony T. Tu, Marcel Dekker, Inc. New York & Basel, "Handbook of Natural Toxins",m 2: 513–543.

Fletcher B. Taylor, Jr., et al., Thrombosis Research, "Clots Lysis: Effects of Protein C", 37: 639–649, 1985.

Hector H. Valdiva, et al., Elsevier Science Publishers B.V. (Biomedical Divison) "FEBS Letters", 226(2); 280–284, 1988.

E. Carbone, et al., European Journal of Physiology, "Blocking of the Squid Axon L+ Channel by Noxiustoxin", 408: 423–431, 1987.

Maria Sitges, et al., The Journal of Neuroscience, "NTX-Induced Transmitter Release and K+ Permeability", 6(6): 1570–1574, 1986.

*Primary Examiner*—Lester L. Lee

*Attorney, Agent, or Firm*—Fleit, Jacobson, Cohn, Price, Holman & Stern

[57] ABSTRACT

The invention relates to a novel immunogenic synthetic peptide that is capable of specifically blocking potassium channels of excitable membranes and inducing immunity against an effective lethal dose of Noxiustoxin. The invention also relates to the discovery that the immunogenic and blocking properties of the peptide are severable. Peptides possessing either the immunogenic or the blocking property are disclosed.

3 Claims, 3 Drawing Sheets

SYNTHETIC NOXIUSTOXIN RELATED PEPTIDES

BACKGROUND TO THE INVENTION

The use of toxins as tools in neurophysiological studies began with the discovery of Tetrodotoxin. Thereafter the application of neurotoxins isolated from scorpion venoms has been widely investigated.

More than 110 different polypeptides have been isolated and characterized from the venom of 21 different species of scorpions which exist in different geographical regions of the world.

The chemical structure of many toxins from scorpion venom has been studied and has been found to consist of compact molecules, stabilized 3 to 4 disulphide bridges with two-and-half turns of alpha-helix and three-strand stretch of antiparallel beta sheet which runs parallel to the alpha-helix. These data were obtained by X-ray diffraction and circular dichroism studies. The use of optical rotatory dispersion measurements has shown that some toxins from the venom of *Centruroides noxius* and *Tityus serrulatus* are highly thermostable: they can be boiled for five minutes and still fold back to their original three-dimensional structure, preserving their toxicity. Two families of toxins have been isolated: one with a short chain (approximately 39 amino acid residues) and another with a long chain (61 to 70 amino acid residues).

In order to obtain information on the active site of these peptides, several chemical modifications have been carried out on some known toxins and it has been found that a reduction of the disulphide bridges, a modification of the carboxylic groups and acetylation of amino groups can change their toxicity. This suggests the importance of some amino acids in the toxin's activity.

The applicant has carried out comparative studies into the primary structure of scorpion toxins using the method of metric analysis with which it has established the existence of at least five different groups of toxins with similary homologous amino acid sequences in which the preservation of cysteines in all the toxins studied seems to be very important for the stabilization of the molecules, and hence for their function.

Similarly, the applicant has synthesized polypeptides whose structure is related to the functioning of neurotoxins and which are the basis for the preparation of synthetic vaccines and drugs.

This invention is based on synthetically obtaining polypeptides of the Noxiustoxin type from the scorpion *Centruroides noxius*. This toxin represents only 1% of the scorpion's soluble venom and its effective lethal dose is in the order of 100 g. per 20 gr. of body weight of albino mice. These compounds belong to the short chain peptide family (39 amino acid residues) which are stabilized by three disulphide bridges and block potassium channels from excitable membranes.

SUMMARY OF THE INVENTION

This invention refers to polypeptides with an amino acid sequence similar to that of Noxiustoxin: they consist of a number of amino acids which varys from 9 to 39; offer good immunogenic responses and for this reason are useful in the preparation of an antitoxin scorpion vaccine and some of them, which have the property of blocking potassium channels, can be used in the preparation of new drugs particularly for treatment of illnesses such as cardiac arrhythmias or others which cause alterations at the level of ionic channels.

It is therefore an objective of this invention to provide polypeptides with immunogenic properties, synthesized according to the amino acid sequences of Noxiustoxin with molecular weights in the range of 1,000 to 4,200.

Another objective of this invention is to obtain polypeptides which have the property of blocking potassium ionic channels.

A further objective is to provide polypeptides which are of use in the preparation of drugs and vaccines.

An additional objective of this invention is to provide products which can be used in the treatment of cardiac arrhythmias and/or illnesses which cause alterations to the level of the ionic channels.

These objectives, among others, can be appreciated in greater detail in the following section.

DETAILED DESCRIPTION OF THE INVENTION

Figure 1A:
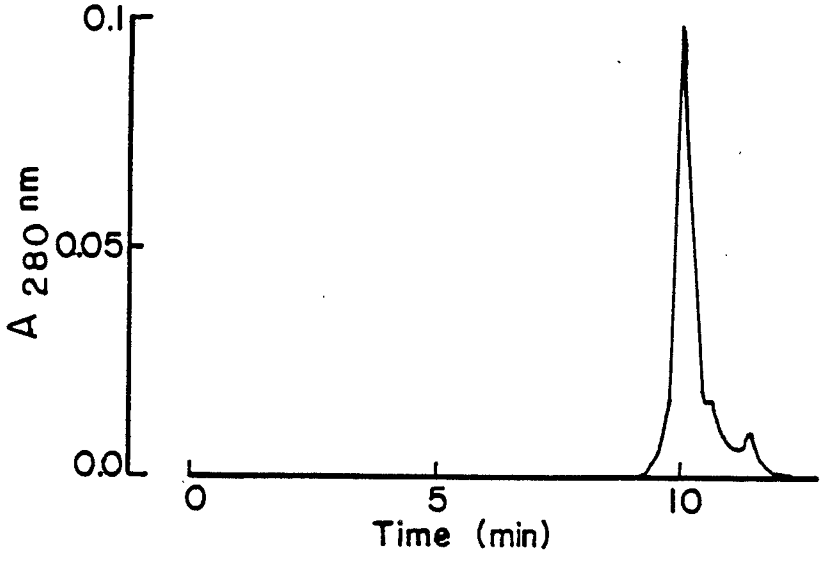
FIG. 1a represents the separation by HPLC of synthetic peptide NTX 1-9 through a molecular weight sieving column (Whatman I-125) in triethylamine-phosphoric acid buffer, pH 2.25, in the presence of acetonitrile (ratio 2:1 by volume), at a flow rate of 1 ml./min.

This invention is related to polypeptides of 9 to 39 amino acids with a similar sequence to that of Noxiustoxin characterized by the applicant with the objective of producing it synthetically by some appropriate method.

The basic sequence synthesized is the following: Threonine-Isoleucine-Isoleucine-Asparagine-Valine-Lysine-Cysteine-Threonine-Serine-Proline-Lysine-Glutamine-Cysteine-Serine-Lysine-Proline-Cysteine-Lysine-Glutamic acid-Leucine-Tyrosine-Glycine-Serine-Serine-Alanine-Glycine-Alanine-Lysine-Cysteine-Methionine-Asparagine-Glycine-Lysine-Cysteine-Lysine-Cysteine-Tyrosine-Asparagine-Asparagine.

Several polypeptides containing a partial amino acid sequence of the basic sequence described above were synthesized.

The results obtained were outstanding due to the fact that polypeptides corresponding to the C-terminal region of the Noxiustoxin sequence present immunogenic properties and have no toxic effect. For this reason they are of use in the preparation of vaccines and/or improvement of the serum used against scorpion stings.

The polypeptides corresponding to the N-terminal region of Noxiustoxin present a toxic effect to mice and block the potassium channels of excitable membranes such as brain synaptosomes, dorsal root ganglion cells and cardiac tissue. These characteristics allow the peptides to be used as tools to study ionic channels or as new drugs for the treatment of illnesses like cardiac arrhythmias involving the potassium channels.

Some examples of synthesized polypeptides are presented below in order to illustrate more fully the objectives of this invention.

I-Synthesis of Peptides with PAM-Resins

The first strategy will be described in detail. In this example the synthesis of polypeptides begins with the preparation of ter-Butyloxycarbonylaminoacil-4-(oximethyl)phenacylacetamidomethyl-resin, abbreviated: BOC-amino acid-PAM-Resin.

(A) Preparation of the Cesium salt of BOC-Asparagine 1.3 millimoles of Boc-Asparagine are dissolved in 0.5 ml. of methanol.

1.43 millimoles of cesium carbonate dissolved in 1 ml. of water are added to this under agitation. The cesium salt of the amino acid formed in this way is concentrated by means of a rotavapor. The water is eliminated using toluene. It is left to dry in vacuum in the presence of phosphorous pentoxide for two hours.

(B) Coupling of the BOC-amino acid with phenacyl bromide ester

The cesium salt of the amino acid is dissolved in 10 ml. of dimethylformamide (DMF) and 1.1 equivalents of phenacyl bromide ester are added for each equivalent amounts of amino acid. The reaction takes place at 50 C. under agitation. The reaction is monitored by means of thin layer chromatography, using the ethyl-acetate:hexane system, with a ratio of 2:3. The product is extracted with 25 ml. of ethyl acetate and is washed twice with water, twice with 5% acetic acid, twice with water, twice with 5% sodium bicarbonate and finally, twice again with water. Anhydrous magnesium sulphate is added to the organic phase to eliminate the residual water. The product is concentrated in a rotavapor.

(C) Reduction with Zinc/Acetic

The amino acid phenacyl ester is dissolved in 30 ml. of 90% glacial acetic acid; 40 parts zinc in powder are added for each part of amino acid and the mixture is left under vigorous agitation. The reaction is monitored by thin layer chromatography using the chloroform-methanol-acetic acid system with a ratio of 10:0.5:0.1. When the reaction is completed, the mixture is filtered through celite and washed five times in 15 ml. of 90% acetic acid; the filtrate is concentrated in a rotavapor and left in a desiccator with phosphorous pentoxide for two hours. The product is dissolved in a mixture of water and ethyl acetate and is washed twice in a saturated solution of sodium chloride. The organic phase is washed twice more with 5% citric acid and the excess is eliminated to a minimum volume and 50 ml. of hexane at 50 C. are added. The mixture is frozen in dry-ice acetone in order to precipitate the product and to decant the hexane which contains acetophenone. This operation is repeated three times in order to eliminate as much acetophenone as possible.

(D) Coupling of the BOC-Asparagine-phenylacetic with amino methyl resin

The amino methyl resin is washed three times with methylene chloride, twice with 5% triethylamine and another three times with methylene chloride. The BOC-Asparagine derivative is dissolved in 10 ml. of DMF plus 20 ml. of methylene chloride and the mixture is added to the amino methyl resin. It is left in agitation for 10 minutes after which 1.3 millimoles of dicyclohexylcarbodiimide (DCC) are added and the product is left under agitation at room temperature for 36 hours.

(E) Acethylation of the free amino groups

In order to block undesirable free amino groups 2 ml. of pyridine and 2 ml. of acetic anhydride are added to the BOC-Asparagine-PAM-resin. After 12 hours of agitation at room temperature the resin is washed three times with methylene chloride, twice with isopropanol and three times with methylene chloride.

(F) Synthesis of the polypeptide

From this moment on, the amino acids (BOC-amino acids) are coupled one by one according to the desired sequence following the steps of deprotection, neutralization and coupling of the Merrifield solid phase technique for synthesizing peptides. The synthesis takes place starting with the amino acid in the C-terminal position and finishing with the amino acid at the N-terminal position. The deprotection of the BOC-amino acid is carried out with 50% trifluoroacetic acid (TFA) in methylene chloride, followed by five washes with methylene chloride. The neutralization step consists of treatment with 5% triethylamine in methylene chloride. The new BOC-amino acids added to the growing chain of the peptide are coupled by means of dicyclohexylcarbodiimide and are also dissolved in methylene chloride.

Normally, for each coupling reaction, the resin is left in agitation at room temperature for two hours. It is immediately washed five times with methylene chloride, twice with isopropanol, twice with methylene chloride, twice with isopropanol and five times with methylene chloride. This constitutes a complete cycle. After each cycle, the reaction is controlled by quantifying the free amino groups according to their reaction with ninhydrin. If there are still free amino groups, a new cycle is repeated with the same amino acid under the same conditions. If free amino groups still remain after completing the third cycle, acethylation of the resin is performed in order to block these groups. The same procedure is followed for the subsequent amino acids from the deprotection step.

II-Synthesis of Peptides with Chloro-methyl-resins

A different strategy has been followed for the synthesis of short-chain polypeptides, in which the steps A, B, C and D above are omitted or modified. Instead, a resin containing chloromethyl groups is used. An example is described for the synthesis of the nonapeptide Threonine from position one to Serine of position nine of Noxiustoxin.

Four millimoles of the first amino acid (BOC-Serine) are dissolved in approximately 2 ml. of methanol and are mixed with two millimoles of cesium carbonate dissolved in 0.3 ml. of water. This is concentrated in a rotavapor and the residual water is removed with toluene (three times, aproximately 5 ml. each time). The product is dried for 12 hours in a desiccator. The cesium salt of the amino acid is dissolved in 8 ml. of dimethylformamide. 2 ml. (aproximately 1 millimole) of this is taken and added to a vial containing 1 gram of chloromethyl-resin (0.67 milliequivalent per gram) suspended in a minimum volume of DMF (aproximately 4 ml.). It is left in a water bath for 17 hours at 50 C.

The resin is transfered to a reaction flask and washed five times with methylene chloride (10 ml. each time). The remaining cesium salt from the amino acid (3 millimoles) in 6 ml. of DMF is mixed with the washed resin and left in agitation at room temperature for 48 hours. The resin is washed twice with DMF, once with DMF and water (ratio 9:1), DMF, once with DMF and ethanol (1:1), once with methylene chloride, once with isopropanol and once with methylene chloride. A sample (usually 1 or 2 mg.) is taken and an amino acid analysis is carried out in order to determine the efficiency of the coupling of the first amino acid. In this example, 0.1 millimole of Serine was obtained for each gram of resin.

After the first amino acid is attached, Merrifield's procedure is followed as described in letter F above.

III. Automatic Synthesis of Polypeptides

A third strategy was also followed for the synthesis of peptides, using commercially available PAM-resins. The entire synthesis is conducted in an Applied Biosystems apparatus, and the Merrifield technique is again used with BOC-amino acids and methylene chloride as solvent and with the use of dicyclocarbodiimide as coupling agent.

After the synthesis of any of the polypeptides, following any of the strategies described above, the peptides are liberated from the resins and purified by high performance liquid chromatography (HPLC), according the following steps:

IV. Cleavage with Fluorhydric Acid

The synthetic peptides are separated from the resins through treatment with fluorhydric acid (gas form). The resin is placed in a teflon container and 90% of acid (by volume) and 10% of anisol are added. The reaction is left for 45 minutes in agitation in an ice-water bath (0 C.). The acid is completely evaporated and the anisol is removed by washing with 100 ml. of ether. The peptide is recovered with 100 ml. of 3% acetic acid. Dithiothreitol, at equimolar concentration, is added to preserve the thiol groups in reduced form. Finally, the peptide is freeze-dried and kept at −20 C. until use.

V. Purification of the Synthetic Peptides

The synthetic peptides are purified by means of HPLC using two types of columns: one column which separates by molecular weight and another of reverse phase (octadecylsilane) using the system of trifluoroacetic acid-acetonitrile.

In order to better illustrate this invention some examples are given below.

Example 1

The polypeptide Threonine-Isoleucine-Isoleucine-Asparagine-Valine-Lysine-Cysteine-Threonine-Serine, corresponding to position one (Threonine) to position nine (Serine) of Noxiustoxin, was synthesized twice according to strategies I and II described above.

Example 2

Following the same strategies, the polypeptide Threonine in position one to Leucine in position twenty of Noxiustoxin (NTX) was synthesized: Threonine-Isoleucine-Isoleucine-Asparagine-Valine-Lysine-Cysteine-Threonine-Serine-Proline-Lysine-Glutamine-Cysteine-Serine-Lysine-Proline-Cysteine-Lysine-Glutamic Acid-Leucine (NTX 1-20).

Example 3

Following strategy I described above, the polypeptide Lysine in position 11 to Asparagine in position 39 of NTX, was synthesized: Lysine-Glutamine-Cysteine-Serine-Lysine-Proline-Cysteine-Lysine-Glutamic Acid-Leucine-Tyrosine-Glycine-Serine-Serine-Alanine-Glycine-Alanine-Lysine-Cysteine-Methionine-Asparagine-Glycine-Lysine-Cysteine-Lysine-Cysteine-Tyrosine-Asparagine-Asparagine (NTX 11-39).

EXAMPLE 4

According to the above mentioned technique, the polypeptide Tyrosine in position 21 to Asparagine 39 of NTX was synthesized: Tyrosine-Glycine-Serine-Serine-Alanine-Glycine-Alanine-Lysine-Cysteine-Methionine-Asparagine-Glycine-Lysine-Cysteine-Lysine-Cysteine-Tyrosine-Asparagine-Asparagine (NTX 21-39).

Example 5

Synthesis of the polypeptide Methionine in position 30 to Asparagine in position 39 of NTX: Methionine-Asparagine-Glycine-Lysine-Cysteine-Lysine-Cysteine-Tyrosine-Asparagine-Asparagine (NTX 30-39).

Example 6

Complete synthesis of Noxiustoxin, from Threonine in position 1 to Asparagine in position 39: Threonine-Isoleucine-Isoleucine-Asparagine-Valine-Lysine-Cysteine-Threonine-Serine-Proline-Lysine-Glutamine-Cysteine-Serine-Lysine-Proline-Cysteine-Lysine-Glutamic Acid-Leucine-Tyrosine-Glycine-Serine-Serine-Alanine-Glycine-Alanine-Lysine-Cysteine-Methionine-Asparagine-Glycine-Lysine-Cysteine-Lysine-Cysteine-Tyrosine-Asparagine-Asparagine (NTX 1-39).

Experimental Data Supporting the Validation of Examples 1 through 6

Once synthesized and liberated from the solid resin, the polypeptides were subjected to amino acid analysis. Table 1 shows the results obtained for the peptides of examples 1 and 5 mentioned above. All synthetic peptides were similarly analyzed.

TABLE 1

Amino Acid Composition of the Synthetic Peptides

| | NTX 1-9 | | NTX 30-39 | |
|---|---|---|---|---|
| Amino Acid | Found | Expected | Found | Expected |
| Aspartic | 1.00 | 1 | 3.00 | 3 |
| Threonine | 1.98 | 2 | —[a] | — |
| Serine | 0.98 | 1 | — | — |
| Glycine | — | — | 0.75 | 1 |
| Valine | 0.85 | 1 | — | — |
| Methionine | — | — | 0.93 | 1 |
| Isoleucine | 1.17 | 2 | — | — |
| Tyrosine | — | — | 0.86 | 1 |
| Lysine | 0.96 | 1 | 1.80 | 2 |
| Cysteine | N.D.[b] | 1 | N.D. | 2 |
| Yield of synthesis | 99% | | 64.3% | |

[a]amino acid absent from the sequence.
[b]N.D. not determined.

The data reported in Table 1 show that the amino acid analysis of synthetic peptides closely related the expected composition. However, all polypeptides were purified by high performance liquid chromatography as shown for NTX 1-9 in FIGS. 1*a*. and *b*. FIG. 1*a*. is an example of separation in a molecular weight sieving column.

Basically only one type of molecular weight peptide (nonapeptide) was found, indicating that the appearance of dimers through disulphide bridge formation did not take place.

Figure 1B:
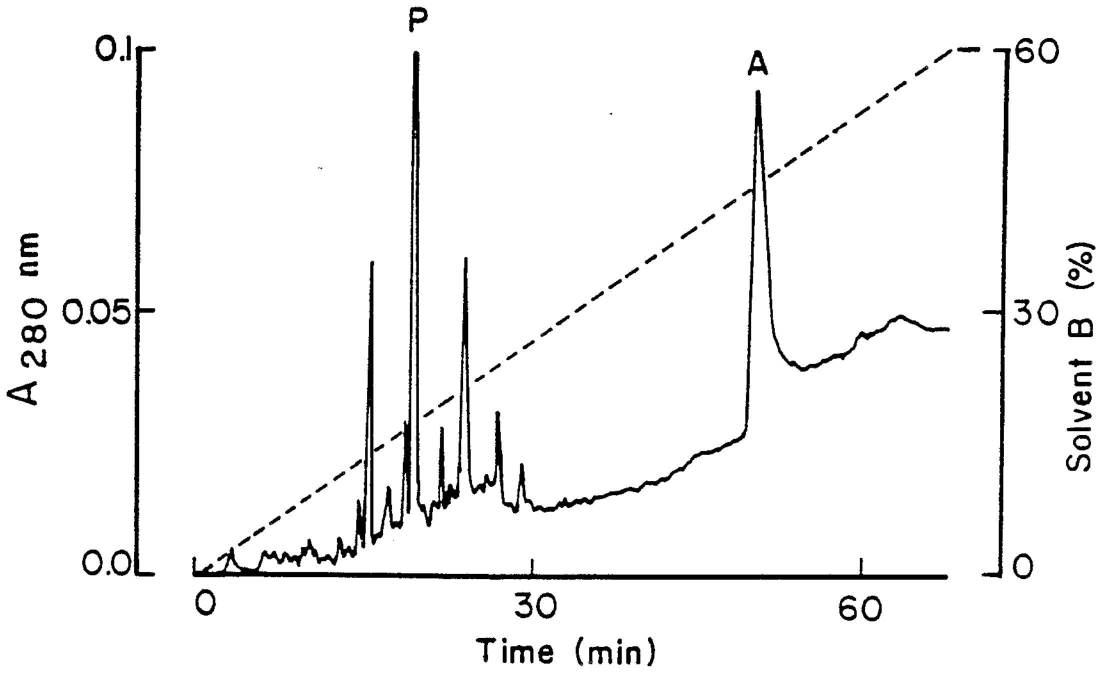
FIG. 1b represents separation by HPLC of synthetic peptide NTX 1-9 through a C18 reverse phase column. A gradient from 100% A (0.12% trifluoroacetic acid (TFA) in water) to 60% B (0.12% TFA in acetonitrile) was run for 70 minutes with a flow rate of 1 ml./min. 50 μg of peptide was applied to the column. The peak on the elution profile labeled "P" is pure NTX 1-9 and that labeled "A" is an artifact of the solvent wash.

In FIG. 1*b* an example of separation of peptide NTX 1-9 by HPLC in a reverse phase column is given. The major peak, P in the figure, corresponds to the expected peptide as verified by direct sequence analysis. A in FIG. 1*b* corresponds to the solvent artefact. Several contaminants were present in the original sample, indicating the need for purification after synthesis.

The mechanism of action of all synthetic peptides was verified by three independent essays: "in vivo" challenge by injection of albino mice (strain CD1) with different amounts of synthetic peptides; liberation of radioactive (tritiated) gamma-amino-butyric acid from mouse brain synaptosomes; and confirmation of the results with electrophysiological experiments, through voltage-clamp technique, in chick embryo dorsal root ganglion cells maintained in "in vitro" culture.

Table 2 shows some of the results obtained with "in vivo" essay for toxicity of the peptides in mice. The synthetic polypeptides were injected via three different routes of administration: intraperitoneal, intraventricular and subcutaneous. The NTX 1-39, NTX 1-9 and NTX 30-39 peptides were soluble in up to at least 10 mg./ml. of water, while the NTX 1-20 required the presence of organic solvents such as 4% of dimethylsulfoxide in order to achieve complete solubilization. The tests for toxicity were also carried out with peptides coupled to mouse serum albumin. The first important observation is that the mouse injected with the synthetic nonapeptide NTX 1-9 showed symptoms of intoxication similar to those observed with native NTX, while the decapeptide NTX 30-39 was not toxic.

The second important observation is that the intoxication symptoms were dose dependent. A dose of 40 g of native NTX per 20 grams of mouse body weight causes hyperexcitability, lacrimation, salivation, dysnea, convulsions and generally produces death as a result of respiratory paralysis or cardiac arrest. Many of these symptoms were observed in several mice injected with 200 g of the peptide NTX 1-9. The symptoms depended on the route of administration: the subcutaneous injection was less toxic than the intraperitoneal or intraventricular ones and the intraventricular injection was the most effective. It is also worth noting that the peptide NTX 1-20 was shown to be toxic. The polypeptides from NTX 21-39 and NTX 30-39, corresponding to the carboxyl-terminal region of the native toxin, were not toxic even when a greater dose of these polypeptides were injected than of polypeptides from the amino-terminal region of Noxiustoxin (NTX 1-9, NTX 1-20).

TABLE 2

Lethality Tests of Synthetic Peptides[a]

| Peptide (dose g) | Administration Route: Intraperitoneally | Subcutaneously | Intraventricularly |
|---|---|---|---|
| NTX 1-9 (200) | Intoxication symptoms within 20 min. Death | Intoxication symptoms within 20 min., hyperexcitability, lacrimation, survived | Intoxication symptoms convulsions within 12 min. Death before 20 min. |
| NTX 1-9 (100) | Doubtful symptoms | No symptoms | Toxic, death within 20 h. |
| NTX 1-9 (20) | No symptoms | No symptoms | Slightly different symptoms to native NTX, survived. |
| MSA-NTX 1-9[b] (100) | Deadly | Deadly | Not tested |
| NTX 1-20 (200) | Deadly | Not tested | Not tested |
| NTX 30-39 (400) | No symptoms | No symptoms | No symptoms |
| MSA-NTX 30-39 (200) | No symptoms | No symptoms | Not tested |
| Native NTX (40) | Toxic | Toxic | Toxic |

[a]All tests were carried out with mice of 20 grams body weight.
[b]MSA means mouse serum albumin coupled to peptide with carbodiimide.

Due to the fact that direct observation of the behaviour of animals injected "in vivo" (intoxication symptoms) with native NTX and/or synthetic polypeptides is dependent upon a subjective evaluation on behalf of the observer, and also poses limits to a more rigorous pharmacokinetic study of these polypeptides, it was decided to confirm the above data with direct measurements in an "in vitro" system. Two strategies were used: quantification of neurotransmitter release from brain synaptosomes and evaluation of ionic currents in excitable cells.

Figure 2:
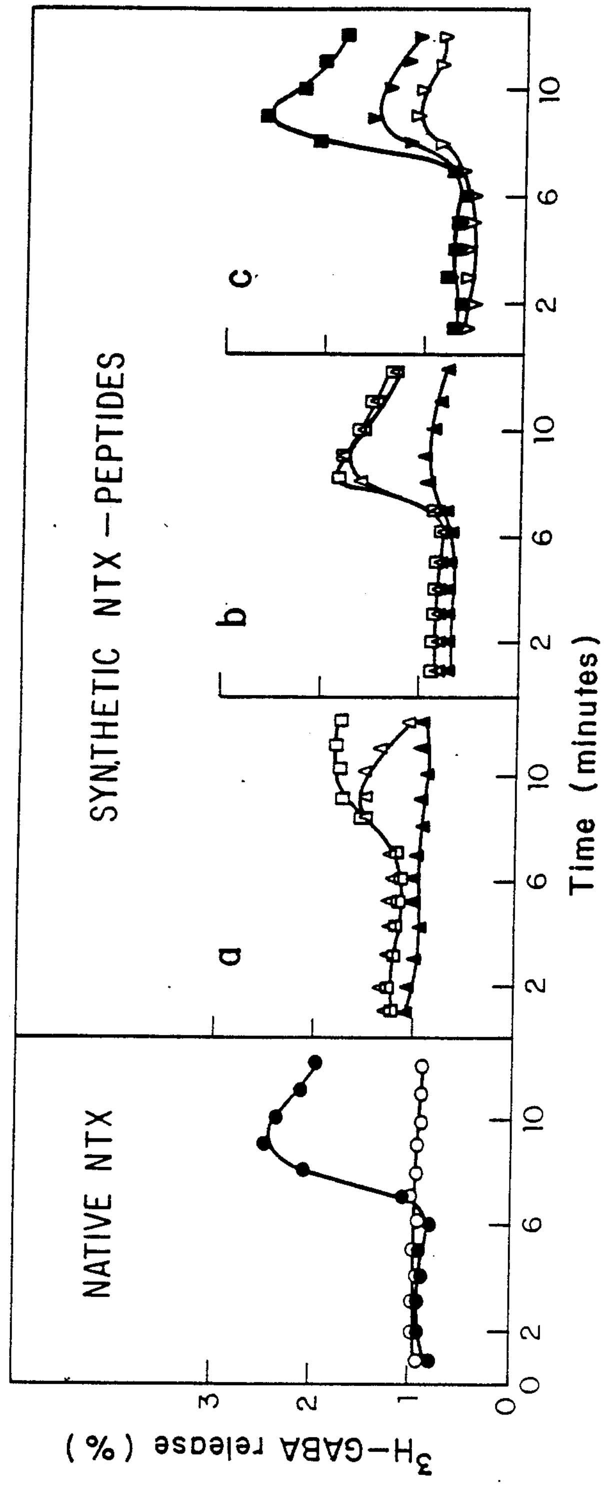
FIG. 2 depicts the effect of native Noxiustoxin and the synthetic peptides on GABA release from Brain Synaptosomes.

In the experiments involving release of neurotransmitters, mouse brain synaptosomes were preloaded with radioactive gamma-amino-butyric acid (2, 3, 3H-GABA) and were placed in Millipore filters (0.65 m) in perfusion chambers, each one containing 0.2 to 0.3 mg. of synaptosomal protein. The fractions from the perfusate (0.5 ml. each) were collected by means of a peristaltic pump at one minute intervals. After 6 minutes, a solution containing synthetic polypeptides was added to the experimental chambers and the radioactivity release was counted in an apparatus for measuring radioisotopes. FIG. 2 shows some representative results obtained by this method. The liberation of GABA per minute is expressed as a percentage of the total radioactivity present in the synaptosomes at the beginning of the experiment. Native NTX, as well as both the N-terminal polypeptides: NTX 1-9 and NTX 1-20, increases neurotransmitter release by blocking potassium permeability, while the polypeptides corresponding to the C-terminal region of NTX are not effective. The total synthetic NTX 1-39 also blocks potassium permeability. Generally, the dose of synthetic polypeptides required for a positive blockade were greater than those of the native toxin, hence confirming the data obtained with the "in vivo" experiments by injecting mice.

In order to corroborate these data by an independent method, the voltage-clamp technique was applied to study potassium channel blockade in neurons from the dorsal root ganglion cells of chick embryo. The results obtained with this system indicate that there is a decrease of at least 30% in the potassium currents when the peptide NTX 1-9 at a concentration of 40 micromolar is added to the tissue culture. On the contrary, when concentrations of up to 100 micromolar of the polypeptide NTX 30-39 are applied to the ganglion cells, there is no change in the potassium currents whose behaviour is the same as in the case of the control experiments.

Figure 3:
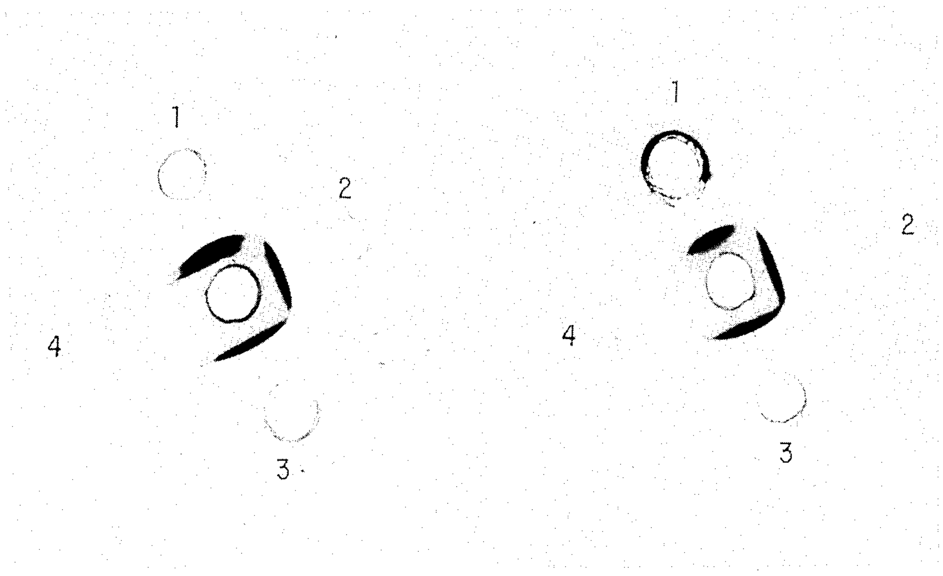
FIG. 3 shows the result of immunodiffusion on 0.8% agarose gel in phosphate-saline buffer.

FIG. 3 shows results of immunodiffusion of the synthetic NTX 1-39 peptide against serum obtained from BALB/c mice that had been immunized for two months with the peptides NTX 1-39, NTX 21-39, NTX 30-39, or with each of these peptides coupled to mice serum albumin (MSA) as a carrier molecule. A group of ten mice were immunized with each peptide and a second group of mice were immunized with each peptide coupled to mouse serum albumin as a carrier molecule. In the experiments depicted in FIG. 3 1 mg./ml of NTX 1-39 coupled to MSA was applied in both central wells. In the experiment on the left side of the Figure well 1 contained antiserum obtained from mice that were immunized with synthetic peptide NTX 30-39 coupled to MSA; well 2 contained antiserum prepared against NTX 21-39-MSA, well 3 contained antiserum prepared against NTX 1-39-MSA, and well 4 contained phosphate-saline buffer as a control. In the experiment depicted on the right side of the Figure well 1 contained antiserum prepared against NTX 30-39, well 2 contained antiserum prepared against NTX 21-39, well 3 contained antiserum against NTX 1-39, and well 4 contained buffer as a control. From the results of the experiments depicted in FIG. 3, it can be concluded that NTX 1-39, NTX 21-39, and NTX 30-39 are immunogenic.

Furthermore, when the group of mice immunized with the total synthetic NTX was challenged "in vivo" with an effective lethal dose of Noxiustoxin (150 g per mouse) more than 75% of the population survived. These data indicate that synthetic polypeptides can be used to obtain serum against scorpion toxins.

The experimental data obtained with synthetic polypeptides corresponding to the total or partial amino acid sequence of Noxiustoxin allows the applicant to claim the following inventions:

What is claimed is:

1. A peptide that is capable of specifically blocking the potassium channels of excitable membranes consisting of the following amino acid sequence: Threonine-Isoleucine-Isoleucine-Asparagine-Valine-Lysine-Cysteine-Threonine-Serine.

2. An immunogenic peptide consisting of the following amino acid sequence: Tyrosine-Glycine-Serine-Serine-Alanine-Glycine-Alanine-Lysine-Cysteine-Methionine-Asparagine-Glycine-Lysine-Cysteine-Lysine-Cysteine-Tyrosine-Asparagine-Asparagine.

3. An immunogenic peptide consisting of the following amino acid sequence: Methionine-Asparagine-Glycine-Lysine-Cysteine-Lysine-Cysteine-Tyrosine-Asparagine-Asparagine.

* * * * *